US00PP20768P2

(12) United States Plant Patent
Westhoff

(10) Patent No.: US PP20,768 P2
(45) Date of Patent: Feb. 23, 2010

(54) ***LOBELIA* PLANT NAMED 'WESLOTI'**

(50) Latin Name: *Lobelia erinus*
Varietal Denomination: Wesloti

(75) Inventor: Heinrich Westhoff, Südlohn (DE)

(73) Assignee: Gartenbau und Spezialkulturen Westhoff GbR, Südlohn (DE)

( * ) Notice: Subject to any disclaimer, the term of this patent is extended or adjusted under 35 U.S.C. 154(b) by 0 days.

(21) Appl. No.: 12/291,385

(22) Filed: Nov. 7, 2008

(51) Int. Cl.
*A01H 5/00* (2006.01)

(52) U.S. Cl. ..... Plt./451

(58) Field of Classification Search ..... Plt./451
See application file for complete search history.

*Primary Examiner*—Kent L Bell
(74) *Attorney, Agent, or Firm*—C. A. Whealy

(57) ABSTRACT

A new and distinct cultivar of *Lobelia* plant named 'Wesloti', characterized by its compact, spherical and somewhat trailing plant habit; vigorous growth habit; freely branching habit and short internodes; dense and bushy plant form; densely pubescent leaves; continuously and freely flowering habit; and intense blue and white bi-colored flowers.

1 Drawing Sheet

Botanical designation: *Lobelia erinus*.
Cultivar denomination: 'Wesloti'.

BACKGROUND OF THE INVENTION

The present invention relates to a new and distinct cultivar of *Lobelia* plant, botanically known as *Lobelia erinus* and hereinafter referred to by the name 'Wesloti'.

The new *Lobelia* plant is a product of a planned breeding program conducted by the Inventor in Südlohn, Germany. The objective of the breeding program is to create new *Lobelia* cultivars with good vigor and attractive flower coloration.

The new *Lobelia* plant originated from a cross-pollination made by the Inventor in July, 2004 of *Lobelia erinus* 'Wesloarc', disclosed in U.S. Plant Pat. No. 15,871, as the female, or seed, parent with a proprietary seedling selection of *Lobelia erinus* identified as code number 04P912, not patented, as the male, or pollen, parent. The new *Lobelia* was discovered and selected by the Inventor as a single flowering plant with the progeny of the stated cross-pollination grown in a controlled greenhouse environment in Südlohn, Germany in June, 2005.

Asexual reproduction of the *Lobelia* plant by vegetative cuttings in Südlohn, Germany since 2005, has shown that the unique features of this new *Lobelia* are stable and reproduced true to type in successive generations.

SUMMARY OF THE INVENTION

Plants of the new *Lobelia* have not been observed under all possible environmental conditions. The phenotype may vary somewhat with variations in environment such as temperature and light intensity without, however, any variance in genotype.

The following traits have been repeatedly observed and are determined to be the unique characteristics of 'Wesloti'. These characteristics in combination distinguish 'Wesloti' as a new and distinct cultivar of *Lobelia:*

1. Compact, spherical and somewhat trailing plant habit.
2. Vigorous growth habit.

3. Freely branching habit and short internodes; dense and bushy plant form.
4. Leaves covered with dense pubescence.
5. Continuously and freely flowering habit.
6. Blue and white bi-colored flowers.

Plants of the new *Lobelia* differ from plants of the female parent, 'Wesloarc', in the following characteristics:

1. Plants of the new *Lobelia* are more compact and trialing in growth habit than plants of 'Wesloarc'.
2. Plants of the new *Lobelia* have thinner stems than plants of 'Wesloarc'.
3. Plants of the new *Lobelia* have smaller leaves than plants of 'Wesloarc'.
4. Plants of the new *Lobelia* have darker blue-colored flowers than plants of 'Wesloarc'.
5. Plants of the new *Lobelia* have smaller sepals than plants of 'Wesloarc'.

Plants of the new *Lobelia* differ from plants of the male parent selection in the following characteristics:

1. Plants of the new *Lobelia* are not as trailing in growth habit as plants of the male parent selection.
2. Plants of the new *Lobelia* have thicker stems than plants of the male parent selection.
3. Plants of the new *Lobelia* have larger flowers than plants of the male parent selection.

Plants of the new *Lobelia* can be compared to plants of *Lobelia erinus* 'Weslospot', disclosed in U.S. Plant Pat. No. 15,835. In side-by-side comparisons conducted in Südlohn, Germany, plants of the new *Lobelia* differed from plants of 'Weslospot' in the following characteristics:

1. Plants of the new *Lobelia* had thinner stems than plants of 'Weslospot'.
2. Plants of the new *Lobelia* had smaller leaves than plants of 'Weslospot'.
3. Plants of the new *Lobelia* had darker blue-colored flowers than plants of 'Weslospot'.
4. Plants of the new *Lobelia* had shorter and broader sepals than plants of the 'Weslospot'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Lobelia*.

The photograph at the top of the sheet comprises a side perspective view of a typical flowering plant of 'Wesloti' grown in a container.

The photograph at the bottom of the sheet is a close-up view of typical flowers and flower buds of 'Wesloti'.

DETAILED BOTANICAL DESCRIPTION

Plants used for the aforementioned photographs and following description were grown under conditions which closely approximate commercial production conditions during the summer in a glass-covered greenhouse in Südlohn, Germany for 27 to 30 weeks in containers. During the production of the plants, day temperatures ranged from 20° C. to 25° C., night temperatures ranged from 16° C. to 18° C. and light levels ranged from 3,000 lux to 50,000 lux. Plants were pinched two times. In the following description, color references are made to The Royal Horticultural Society Colour Chart, 2001 Edition, except where general terms of ordinary dictionary significance are used.

Botanical classification: *Lobelia erinus* 'Wesloti'.

Parentage:

*Female parent.*—*Lobelia erinus* 'Wesloarc', disclosed in U.S. Plant Pat. No. 15,871.

*Male parent.*—Proprietary seedling selection of *Lobelia erinus* identified as code number 04P912, not patented.

Propagation:

*Type cutting.*—Vegetative cuttings.

*Time to initiate roots, summer.*—About 10 to 14 days at 20° C.

*Time to initiate roots, winter.*—About 16 to 18 days at 20° C.

*Time to produce a rooted young plant, summer.*—About 21 to 24 days at 20° C.

*Time to produce a rooted young plant, winter.*—About 24 to 26 days at 20° C.

*Root description.*—Fine, fibrous; color, close to 158A.

*Rooting habit.*—Freely branching; moderately dense to dense.

Plant description:

*Form.*—Compact, spherical and somewhat trailing plant habit. Freely branching habit with lateral branches developing at potentially every node; short internodes; dense and bushy plant habit; vigorous growth habit.

*Plant height.*—About 15 cm to 20 cm.

*Plant width.*—About 45 cm.

*Lateral branch description.*—Length: About 15 cm to 25 cm. Diameter: About 1.1 mm to 2.5 mm. Internode length: About 1.2 cm. Strength: Strong, flexible. Texture: Densely pubescent. Color: Close to 146A.

Foliage description:

*Arrangement.*—Alternate, simple; sessile.

*Length, basal leaves.*—About 4.1 cm.

*Width, basal leaves.*—About 1.7 cm.

*Shape.*—Oblanceolate to lanceolate.

*Apex.*—Acute to obtuse.

*Base.*—Attenuate.

*Margin.*—Entire to crenate.

*Texture, upper and lower surfaces.*—Densely pubescent.

*Venation pattern.*—Pinnate; arcuate.

*Color.*—Developing leaves, upper surface: Close to 137A. Developing leaves, lower surface: Close to 147B. Fully expanded leaves, upper surface: Close to 147A; venation, slightly lighter than 147A. Fully expanded leaves, lower surface: Close to 147B; venation, slightly lighter than 147B.

Flower description:

*Flower arrangement/habit/shape.*—Flowers typically arranged in racemes. Flowers held mostly outwardly. Freely and continuously flowering; older flowers are overgrown by new flowers and leaves; typically about seven to ten flowers per lateral branch. Flowers not fragrant. Flowers tubular with three lower petals and two upper petals.

*Natural flowering season.*—April until frost in the Germany.

*Flower longevity on the plant.*—Longevity of individual flowers is highly dependent on weather conditions; typically about one week; flowers not persistent.

*Inflorescence height.*—About 16 cm to 24 cm.

*Inflorescence diameter.*—About 6.5 cm.

*Flower diameter.*—About 1.9 cm.

*Flower depth (height).*—About 2.2 cm.

*Flower throat diameter.*—About 4.2 mm.

*Flower tube length.*—About 1.2 cm.

*Flower tube diameter, at the base.*—About 2.5 mm.

*Flower buds, developing.*—Length: About 1.3 cm. Diameter: About 4.5 mm. Shape: Oblong. Color: Towards the base, close to 145B to 145D; towards the apex, close to 145A to 145B.

*Petals.*—Arrangement: Single whorl of five petals, fused; three larger lower petals and two smaller upper petals. Three lower petals: Length, above throat: About 1.1 cm. Width: About 6.5 mm. Shape: Obovate. Apex: Slightly cuspidate. Margin: Entire. Texture, upper and lower surfaces: Smooth, glabrous. Two upper petals: Length, above throat: About 7 mm. Width: About 2.3 mm. Shape: Oblanceolate. Apex: Slightly cuspidate. Margin: Entire. Texture, upper and lower surfaces: Smooth, glabrous. Color, upper and lower petals: When opening, upper surface: Close to 98A; towards the base, close to 155C. When opening, lower surface: Close to 98B to 98C; towards the base, close to 155C. Fully opened, upper surface: Close to 98A to 98B; towards the base, close to 155C. Color becoming closer to 98B to 98C with development. Fully opened, lower surface: Close to 98C to 98D; towards the base, close to 155C. Color becoming closer to 97B to 97D. Throat: Close to 155D; venation, close to N144A. Tube: Close to 98A; venation, close to N144B. Eye: Close to 155lC; six stripes, close to 99A; two small spots, close to 144A.

*Sepals.*—Arrangement: Single whorl of five sepals, fused at the base; star-shaped calyx. Length: About 5.5 mm. Width: About 1.4 mm. Shape: Narrowly deltoid. Apex: Acute. Margin: Entire. Texture, upper and lower surfaces: Pubescent. Color, upper and lower surfaces: Close to 137A to 137B.

*Peduncles.*—Length: About 12 cm to 18 cm. Diameter: About 1.1 mm. Strength: Strong, flexible. Texture: Pubescent. Color: Close to 137A.

*Pedicels.*—Length: About 1.2 cm to 2 cm. Diameter: About 0.8 mm. Strength: Strong, flexible; wiry. Texture: Pubescent. Color: Close to 137A.

*Reproductive organs.*—Stamens: Quantity per flower: About five. Filament length: About 8 mm. Filament color: Towards the base, close to 155C; towards the apex, close to N89B. Anther length: About 3.2 mm. Anther width: About 2 mm. Anther color: Close to N186A. Pollen amount: Moderate. Pollen color: Close to 9A. Pistils: Quantity per flower: One. Pistil length: About 1.2 cm. Stigma shape: Ovate. Stigma color: Close to 83B to 83A. Style length: About 8 mm. Style color: Close to 144C to 144D. Ovary color: Close to 137A.

*Seeds.*—Length: Less than 0.5 mm. Diameter: Less than 0.5 mm. Color: Close to 187A.

Disease/pest resistance: Plants of the new *Lobelia* have not been noted to be resistant to pathogens and pests common to *Lobelia.*

Temperature tolerance: Plants of the new *Lobelia* have been observed to tolerate temperatures from about 6° C. to about 32° C.

It is claimed:

1. A new and distinct *Lobelia* plant named 'Wesloti' as illustrated and described.

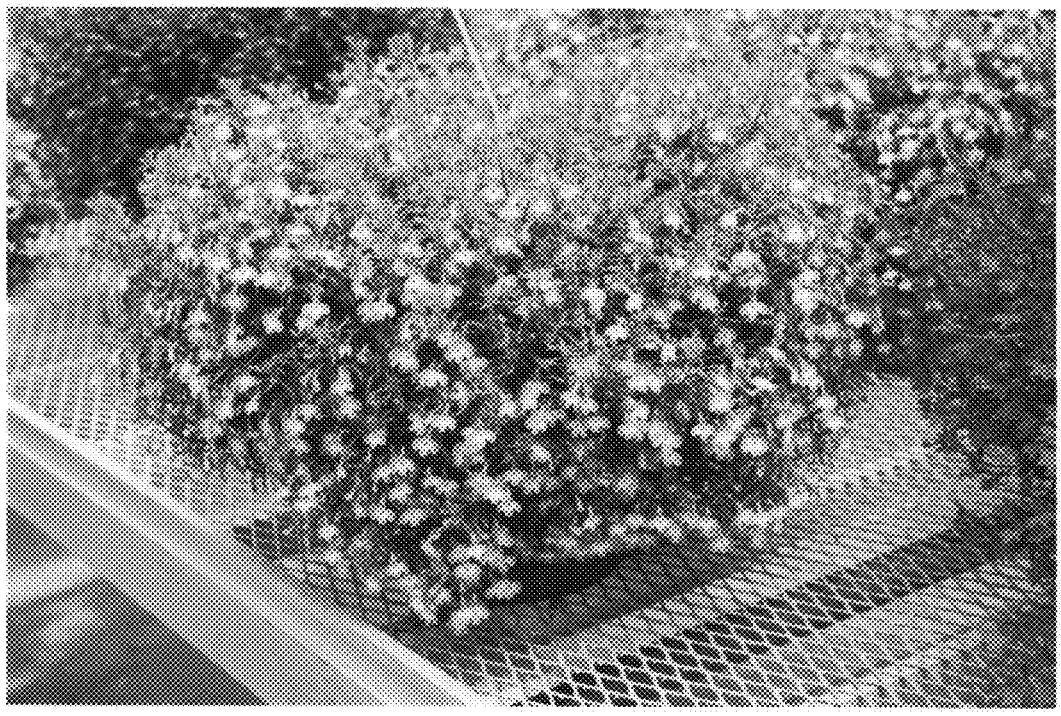
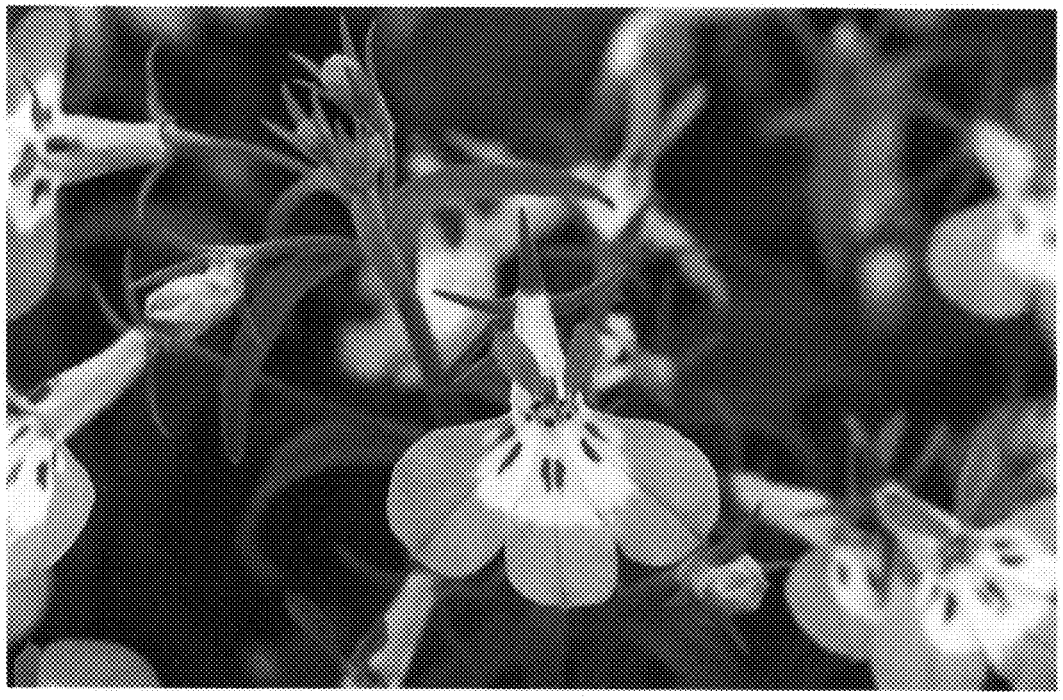

* * * * *